(12) United States Patent
Bibb et al.

(10) Patent No.: US 7,807,381 B2
(45) Date of Patent: Oct. 5, 2010

(54) METHODS FOR ASSESSING CDK5 ACTIVATION AND FUNCTION

(75) Inventors: James A. Bibb, Dallas, TX (US); Ammar H. Hawasli, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 571 days.

(21) Appl. No.: 11/754,097

(22) Filed: May 25, 2007

(65) Prior Publication Data

US 2008/0293073 A1    Nov. 27, 2008

(51) Int. Cl.
*G01N 33/53* (2006.01)
(52) U.S. Cl. .................. 435/7.1; 435/7.2; 435/7.8; 435/7.92
(58) Field of Classification Search .................. None
See application file for complete search history.

(56) References Cited

OTHER PUBLICATIONS

Nath et al, Biochemical Biophysical Res. Comm., vol. 274, 2000, pp. 16-21.*
Alvira et al., J. Pineal Res., vol. 40, Apr. 2006, pp. 251-258.*
Angelo et al., "Cyclin-dependent kinase 5 in synaptic plasticity, learning and memory," *J. Neurochem.* 99:353-70, 2006.
Bibb et al., "Phosphorylation of protein phosphatase inhibitor-1 by Cdk5," *J. Biol. Chem.* 276:14490-14497, 2001.
Bibb et al., "Phosphorylation of DARPP-32 by Cdk5 modulates dopamine signalling in neurons," *Nature* 402:669-71, 1999.
Bibb et al., "Effects of chronic exposure to cocaine are regulated by the neuronal protein Cdk5," *Nature* 410:376-80, 2001.
Bibb, "Role of Cdk5 in neuronal signaling, plasticity, and drug abuse," *Neurosignals* 12:191-199, 2003.
Cheung et al., "Synaptic roles of Cdk5: implications in higher cognitive functions and neurodegenerative diseases," *Neuron* 50:13-18, 2006.
Cruz and Tsai, "A Jekyll and Hyde kinase: roles for Cdk5 in brain development and disease," *Curr. Opin. Neurobiol.* 14:390-394, 2004.
Cruz et al.,"Aberrant Cdk5 activation by p25 triggers pathological events leading to neurodegeneration and neurofibrillary tangles," *Neuron* 40:471-83, 2003.
Fischer et al., "Opposing roles of transient and prolonged expression of p25 in synaptic plasticity and hippocampus-dependent memory," *Neuron* 48:825-38, 2005.
Guo, "Cyclin-dependent kinase 5—a neuronal killer?," *Sci. Aging Knowledge Environ.*, 50:36, 2003.
Hawasli et al., "Cyclin-dependent kinase 5 governs learning and synaptic plasticity via control of NMDAR degradation," *Nature Neurosci.*, 10:880-6, 2007.
Kusakawa et al.,"Calpain-dependent proteolytic cleavage of the p35 cyclin-dependent kinase 5 activator to p25," *J. Biol. Chem.* 275:17116-172, 2000.
Lee et al., "Neurotoxicity induces cleavage of p35 to p25 by calpain," *Nature* 405:360-364, 2000.
Liu et al., "Comparing calpain- and caspase-3-mediated degradation patterns in traumatic brain injury by differential proteome analysis," *Biochem. J.* 394:715-25, 2006.
Lynch et al.,"LTP consolidation: substrates, explanatory power, and functional significance," *Neuropharmacol.* 52:12-23, 2007.
Nguyen and Bibb, "Cdk5 and the mystery of synaptic vesicle endocytosis," *J. Cell. Biol.* 163:697-99, 2003.
Nguyen et al., "Regulation of protein phosphatase inhibitor-1 by cyclin-dependent Kinase 5," *J. Biol. Chem.*, 282:16511-16520, 2007.
Nguyen et al., "Differential regulation of the CdkS-dependent phosphorylation sites of inhibitor-1 and DARPP-32 by depolarization," *J. Neurochem.*, 103:1582-1593, 2007.
Sahin and Bibb, "Protein kinases talk to lipid phosphatases at the synapse," *Proc. Nat'l Acad. Sci. USA* 101:112-113, 2004.

* cited by examiner

*Primary Examiner*—Jeffrey Stucker
*Assistant Examiner*—Stephen Gucker
(74) *Attorney, Agent, or Firm*—Fulbright & Jaworski

(57) ABSTRACT

As described herein, signaling events occurring in neurons or at neuronal synapses have been identified that involve Cdk5 and various other molecules which bind to, are activated by, and/or activate Cdk5. Of particular relevance are interactions that stimulate calpain cleavage of p35 into p25, which binds Cdk5 in pathologic states. Assays to identify modulators of these interactions are provided.

6 Claims, 6 Drawing Sheets

METHODS FOR ASSESSING CDK5 ACTIVATION AND FUNCTION

This invention was made with government support under R01 DA016672-01 awarded by NIH National Institute of Drug Abuse. The government has certain rights in the invention.

BACKGROUND OF THE INVENTION

1. Field of the Invention

The present invention relates to the fields of molecular biology, neurobiology and pathophysiology. More specifically, it deals with the identification of a molecular interaction between Cdk5 and various other molecules present at synapses and/or in neurons. The present invention also provides for methods of identifying agents that alter these interactions.

2. Description of Related Art

Cognitive impairment due do dementia constitutes a major symptom in patients suffering from neurodegenerative diseases such as Alzheimer's disease, vascular dementia, mixed dementia, and Parkinson's disease. Alzheimer's disease, which accounts for approximately half of all dementia cases, afflicts over 5.1 million Americans. Without additional therapeutics, it is estimated that by 2050, 11 to 16 million patients will suffer from Alzheimer's disease. Major neuropsychiatric disorders including attention deficit hyperactivity disorder (ADHD) and post-traumatic stress disorder (PTSD) also involve disorders in cognition and aversive memory.

Recent advances in the fields of behavioral neuroscience and synaptic plasticity have extended our understanding of learning and memory and provide a basis for the development of new therapeutics. Current data demonstrates that information is processed and stored in neuronal compartments, synapses. Upon membrane depolarization, neurotransmitters activate specific receptors and trigger an array of biochemical events in the post-synaptic compartment. These biochemical intracellular signal transduction pathways lead to modifications in numerous targets including ion channels, neurotransmitter receptors, and gene transcription factors, which then modulate the strength of these synapses. Modulation of synaptic strength (i.e. synaptic plasticity) is thought to be the key component by which learning and memory occurs. However, the particular pathways that contribute to normal synaptic events, as well as those that participate in the parallel disease states, remain to be determined.

SUMMARY OF THE INVENTION

Thus, as described herein, there is provided a method of identifying an inhibitor of Cdk5/p25 complex formation comprising (a) providing a system that permits formation of Cdk5/p25 complex formation; (b) introducing into the system a candidate substance; and (c) assessing Cdk5/p25 complex formation using a p25 selective antibody, wherein a candidate substance that reduces Cdk5/p25 complex formation, as compared to Cdk5/p25 complex formation observed in the absence of the candidate substance, identifies the candidate substance as an inhibitor of Cdk5/p25 formation. The system may be a cell-free system or a cell-based system, such systems based on a cell selected from the group consisting of continuously dividing cells in culture, primary cultures of neurons derived from animal brain tissue, or neurons either acutely dissociated or occurring in intact brain tissue. Assessing may comprise Western blot or ELISA.

In another embodiment, there is provided a method of identifying an inhibitor of calpain-dependent p25 formation comprising (a) providing a system that permits cleavage of p35 into p25 by calpain; (b) introducing into the system a candidate substance; and (c) assessing p25 formation using a p25 selective antibody, wherein a candidate substance that reduces p25 formation, as compared to p25 formation observed in the absence of the candidate substance, identifies the candidate substance as an inhibitor of calpain-dependent p25 formation. The system may be a cell-free system or a cell-based system, such systems based on a cell selected from the group consisting of continuously dividing cells in culture, primary cultures of neurons derived from animal brain tissue, or neurons either acutely dissociated or occurring in intact brain tissue. Assessing may comprise Western blot or ELISA.

In yet another embodiment, there is provided a method of identifying an inhibitor of calpain activation comprising (a) providing a system comprising calpain and Cdk5; (b) introducing into the system a candidate substance; and (c) assessing Cdk5/caplain complex formation or calpain proteolytic activity, wherein a candidate substance that reduces Cdk5/calpain complex formation or calpain proteolytic activity, as compared to Cdk5/calpain complex formation or calpain proteolytic activity observed in the absence of the candidate substance, identifies the candidate substance as an inhibitor of calpain activation. The system may be a cell-free system or a cell-based system, such systems based on a cell selected from the group consisting of continuously dividing cells in culture, primary cultures of neurons derived from animal brain tissue, or neurons either acutely dissociated or occurring in intact brain tissue. Assessing may comprise (a) measuring Cdk5 binding to calpain; or (b) measuring calpain proteolytic activity. Assessing may comprise Western blot, gel mobility shift, FRET, BRET, protein pull-down, or ELISA-based detection of complex formation. The proteolytic activity may be measured by assessing calpain cleavage of spectrin, NR2B, Jun, PSD-95 or any other protein in the calpain degradome, and may further comprise Western blotting or ELISA for the reduction in a calpain substrate, or the formation of cleaved forms of a calpain substrate.

In still yet another embodiment, there is provided a method of identifying an inhibitor of Cdk5-NR2B complex formation comprising (a) providing a system comprising NR2B and Cdk5; (b) introducing into the system a candidate substance; and (c) assessing Cdk5/NR2B complex formation or reduces Cdk5 phosphorylation activity, wherein a candidate substance that reduces Cdk5/NR2B complex formation or reduces Cdk5 phosphorylation activity, as compared to Cdk5/NR2B complex formation or reduces Cdk5 phosphorylation activity observed in the absence of the candidate substance, identifies the candidate substance as an inhibitor of Cdk5-NR2B formation or reduction of Cdk5 phosphorylation activity. The system may be a cell-free system or a cell-based system, such systems based on a cell selected from the group consisting of continuously dividing cells in culture, primary cultures of neurons derived from animal brain tissue, or neurons either acutely dissociated or occurring in intact brain tissue. Assessing may comprise gel mobility shift, FRET, BRET, Western blot, protein pull-down, or ELISA-based detection of complex formation. Assessing may comprise (a) measuring Cdk5/NR2B complex formation; or (b) measuring Cdk5 phosphorylation activity.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Cdk5 conditional knockout attenuates calpain cleavage of NR2B in response to NMDA receptor activation in hippocampal slices. Immunoblot of cleaved NR2B is shown (right) with quantiation (left). (FIG. 2B) Addition of Cdk5 activates calpain cleavage of the cytoplasmic domain of NR2B in vitro. Coomassie bands of recombinant NR2B from time-course reactions is shown (top) with quantitation (bottom). $*P<0.05$, $***P<0.01$ (post hoc) student's t-test.

(FIG. 5A) Reduction in phosphorylation of three Cdk5 sites by NMDA. Quantitative immunoblot analyses is shown of acute striatal slices incubated with NMDA for the doses and times indicated, n=3-12. $*p<0.05$; $**p<0.01$ vs. control, one-way ANOVA with Dunnett's multiple comparison test. (FIG. 5B) Inhibition of Cdk5-dependent phosphorylation of inhibitor-1 by NR2B as assessed by time-course (top), dose-response (middle), and Line-Weaver Burke (bottom) analyses of in vitro phosphorylation reactions conducted in the presence of the indicated inhibitors or control proteins.

DESCRIPTION OF ILLUSTRATIVE EMBODIMENTS

Described herein are previously unidentified signaling events. The events generally involve the neuronal protein kinase, Cdk5. These events contribute to learning and memory, synaptic plasticity, and neuropathology, as examples. A targeted disruption of Cdk5 complex formation provides a new classes of therapeutics. The Cdk5 complex may include a form of its activating cofactors (e.g., p35, p25, p39, or p29), the NR2B subunit of the NMDA receptor, or the calcium ($Ca^{2+}$)-dependent protease calpain.

I. Cdk5 Binding and Activity

Cdk5 is an atypical member of the cyclin-dependent kinase family that is dependent upon association with the neuronal specific cofactor p35 for activation. Cdk5 is an atypical member of the cyclin-dependent kinase family that is dependent upon association with the neuronal specific cofactor p35 for activation. It is constitutively active in neurons and is involved in many aspects of neuronal function including corticogenesis (Ohshima et al., 1996), neuromuscular junction formation (Cheung et al. 2006), the synaptic vesicle cycle (Nguyen & Bibb, 2003; Sahin & Bibb, 2004), and dopamine neurotransmission (Bibb, 2003; Bibb et al., 1999; 2001a). It has also been implicated in virtually every form of neurotoxicity and neurodegeneration (Cruz & Tsai, 2004; Guo, 2003). This dual role in health and disease is conferred upon Cdk5 by virtue of the fact that p35 serves is a substrate of the $Ca^{2+}$-dependent protease, calpain (Kusakawa et al., 2000).

Figure 1:
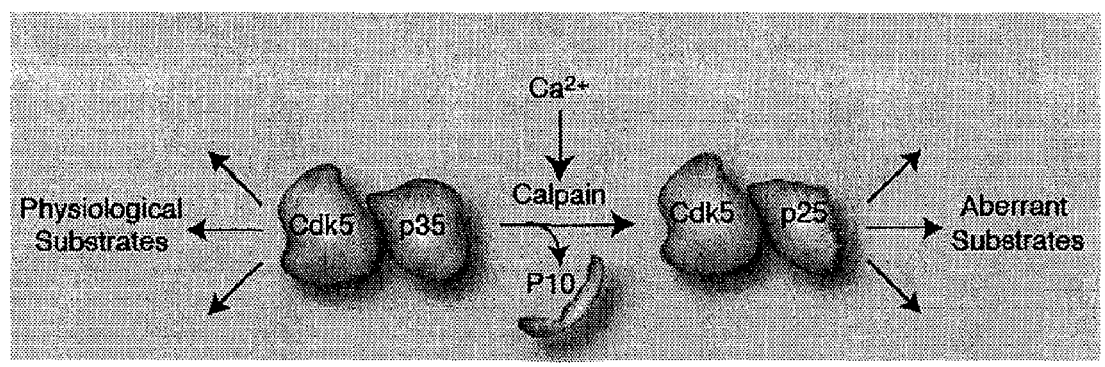
FIG. 1—Schematic of Cdk5 in its physiological and aberrant form.

Under stressful conditions, calpain is activated by elevated intracellular $Ca^{2+}$ and cleaves p35, thereby removing the first 100 amino acids to produce p25 (Lee et al., 2000) (FIG. 1). Cdk5 associated with p25 phosphorylates aberrant substrates leading to cell death. Interestingly, before transgenic overexpression of p25 causes neurodegeneration, it results in a transient improvement in learning and synaptic plasticity (Cruz et al., 2003; Fischer et al., 2005). Using a unique anti-p25 antibody (deposited with ATCC, Manassas, Va., on Jul. 25, 2007; accession no. PTA-8555), developed by the inventors, they have recently found that low levels of p25 are generated at the synapse by physiological glutamatergic neurotransmission. Cdk5 has been suggested to be an important regulator of synaptic plasticity, learning and memory (Angelo et al., 2006), but the mechanisms by which it contributes to this most fundamental feature of brain function have, until now, been unclear.

To better understand the role of Cdk5 in brain function, the inventors derived a conditional knockout (CKO) model system which allows Cdk5 to be ablated in adult animals, thereby avoiding the confounds of perinatal lethality due to congenital abnormalities associated with constitutive knockout of Cdk5 or its activating cofactor, and the non-specificity of pharmacological inhibitors (Hawasli et al., 2007). They found that loss of Cdk5 results in enhanced learning, memory, and synaptic plasticity. The threshold for hippocampal LTP is reduced due to increases in synaptic levels of the NR2B subunit of the NMDA receptor. They found that this effect was due to the fact that Cdk5 activates the $Ca^{2+}$-dependent protease calpain, which normally degrades NR2B in response to excitatory glutamate neurotransmission. Further, they believe that this interaction between Cdk5 and calpain is an important aspect of its function in the CNS. At the same time, they also determined that activated NMDA receptors inhibit Cdk5 (Nguyen et al. 2007a; 2007b), suggesting a bidirectional structural and regulatory relationship between Cdk5 and NMDA receptors at the synapse.

Calpain is the central mediator of changes in extracellular adhesion and intracellular cytoskeletal systems which underlie morphological remodeling associated with synaptic plasticity. In this model, alternations in integrin adhesion molecules direct changes in the actin cytoskeleton (Lynch et al., 2007). This modulation synergizes with excitatory neurotransmission-dependent intracellular $Ca^{2+}$ signaling which activates calpain, causing cleavage of the actin binding factor spectrin. Calpain-cleaved spectrin cross-links and stabilizes polymerized actin filaments which drives and consolidates the morphological changes in the synapse. This remodeling accommodates elaboration of the postsynaptic density (PSD) and elevated levels of PSD-95 and NMDA receptors.

Figure 5:
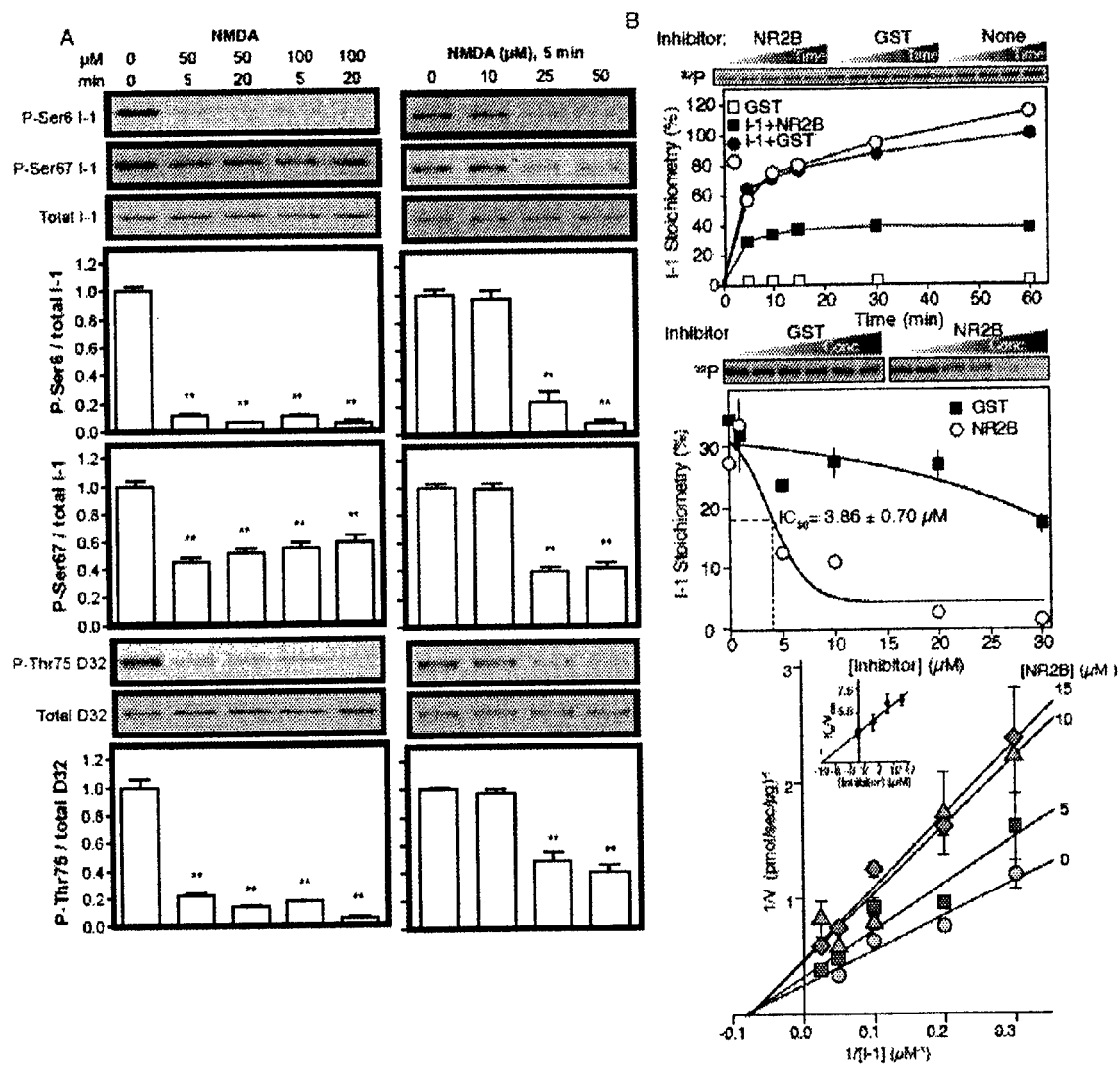
FIGS. 5A-B—NMDA receptor activation inhibits Cdk5 and the cytoplasmic domain is a Cdk5 inhibitor.

Co-immunoprecipitation experiments have demonstrated that Cdk5 bound to NR2B in vivo and in vitro (Liu et al., 2006). Moreover, the inventors demonstrated that Cdk5 is constitutively active under basal conditions (Bibb et al., 1999). In other experiments, they found that activation of NMDA receptors resulted in reduction in Cdk5-dependent phosphorylation of numerous substrates (Nguyen et al., 2007a) (FIGS. 5A-B). To determine if these observations were related, the inventors conducted in vitro phosphorylation reactions with Cdk5 and a test substrate, protein phosphatase inhibitor-1. Addition of the cytoplasmic domain of NR2B to this reaction resulted in a dramatic loss in Cdk5 activity. Kinetic analysis confirmed that the NR2B receptor cytoplasmic domain functions as a potent and selective inhibitor of Cdk5 ($IC_{50}$_4 µM) and indicated a noncompetitive inhibition mechanism. Furthermore, preliminary data suggests that a peptide encompassing amino acid residues 1101-1130 of NR2B may serve as an effective inhibitor of Cdk5. These new data further confirm that NR2B can block Cdk5 activity, and further, that these interactions may be targeted for disruption so that Cdk5 may be uncoupled from NMDA receptors.

II. Screening Methods

Disruption of the activation of calpain by Cdk5 should block key pathways that contribute to synaptic remodeling. As this may be predicted to interfere with the consolodation of learning, it serves as an ideal strategy for treatment of neuropsychiatric disorders that involve learning such as attention deficit hyperactivtiy disorder (ADHD). Indeed, disruption of calpain-Cdk5 interactions is quite likely to attenuate p25 generation, which has been causually linked to neurodegeneration. Disruption of the interaction between calpain and Cdk5 may thus serve as a strategy to treat Alzheimer's disease, tauopathies, and other neurodegenerative disorders that dramatically affect cognition. Furthermore, it would be a key therapeutic for the treatment of post-traumatic stress disorder (PTSD), where the reconsolidation of adversive memories impairs function.

The inventors have additional unpublished data indicating that p25 contributes directly to neurodegeneration following ischemia or reperfusion. Thus, a therapeutic that blocks Cdk5-calpain interactions would also serve as a valuable provolacsis for this major clinical problem and may limit the latent damage that occurs in stroke patients. Finally, inhibition of the Cdk5-calpain interaction may have broader clinical applications outside of neurology, for example, in inhibiting platelet aggregation or degranulation, inhibiting or reverse erythrocyte sickling, inhibiting human immunodeficiency virus infection, and inhibiting unwanted cellular proliferation or migration.

Disruption of NR2B-Cdk5 interactions may represent a more subtle, and therefore specific, but equally important target. A chemical compound with this capability would uncouple the active Cdk5 complex from NMDA receptors and displace calpain from the complex with it. This would be predicted to improve cognition, as proven by observations that disruption of this very interaction by Cdk5 CKO improves learning, memory, and synaptic plasticity. Such a reagent would be very useful in treating cognitive disorders with the same potential of classes of cognitive enhancing agents such as ampakines.

To identify a useful modulator, one generally will determine the ability of a candidate substance to alter the binding and function of Cdk5, calpain. For example, a method generally comprises:

(a) providing a candidate substance;
(b) mixing the candidate substance with Cdk5 and calpain or NR2B; and
(c) measuring the binding of Cdk5 to calpain or NR2B, or Cdk5 or calpain activity, where a difference between the binding or activity observed in step (c), as compared to the binding or activity observed in the absence of the candidate substances, indicates that the substance inhibits complex formation between Cdk5 and calpain or NR2B. Such assays may be conducted in cell free systems, in isolated cells, or in organisms including transgenic animals.

It will, of course, be understood that all the screening methods as described herein are useful in themselves notwithstanding the fact that effective candidates may not be found. The invention provides methods for screening for such candidates, not solely methods of finding them.

A. Modulators/Candidate Substances

As used herein the term "candidate substance" refers to any molecule that may modulate the binding of Cdk5 to NR2B or calpain as evidenced by assessment either of Cdk5 binding to NR2B or calpain, the activity of Cdk5 in the presence of NR2B, the activity of calpain in the presence of Cdk5, or otherwise regulate the activity of Cdk5. The candidate substance may be a protein or fragment thereof, a small molecule, or even a nucleic acid molecule. It may prove to be the case that the most useful pharmacological compounds will be compounds that are structurally related to Cdk5 or its binding partners, for example, peptide fragments of these molecules. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified may be peptide, polypeptide, polynucleotide, small molecule inhibitors or any other compounds that may be designed through rational drug design starting from known inhibitors or stimulators.

In addition to the compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

B. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion or to inhibit the binding of other molecules is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determination of binding. Usually, the target will be the labeled species, decreasing the chance that the labeling will interfere with or enhance binding. Of particular interest here are competitive binding formats can be performed in which one of the agents is labeled, and one may measure the amount of free label versus bound label to determine the effect on binding. Assays for assessing binding include gel mobility shift, FRET, BRET, protein pulldown, or ELISA based detection of complex formation.

A technique for high throughput screening of compounds is described in WO 84/03564. Large numbers of small peptide test compounds are synthesized on a solid substrate, such as plastic pins or some other surface. Bound polypeptide is detected by various methods.

Another example of an in vitro assay is an activity assay. Enzymes catalyze reactions, converting of substrate molecules to products. Direct interactions between the substrates and the specific enzyme of a particular reaction facilitates the alterations that result in product formation. Enzymes may be targeting by molecules that inhibit or enhance their activity. Direct enzyme inhibition is the subject of many successful drug screens. A major feature of signal transduction in the nervous system and elsewhere is modulation of enzymatic activity. In many cases the regulation of an enzyme is accomplished through protein-protein interactions. Thus the regulation of enzyme activity and complex formation are equivocal. Such regulatory mechanisms serve as important specific targets for therapeutic drug development. In such cases, an activity assay must include the detection of the effect of the activating or inhibiting protein and then the ability of candidate substance to interfere with that regulatory effect. An assay designed to detect regulation of enzyme activity and distribution thereof relies upon detection of enzyme activity as reflected in the disappearance of substrate or the accumulation of product. Methods include colorimetric, fluorescent, or radionuclide detection. Substrates or products may be directly detected or indirectly quantitated via immunodetection or some other secondary enzymatic measure. Permutations of enzymatic assays are widely known and numerous.

C. In cyto Assays

As described herein, the inventors contemplate screening of compounds for their ability to modulate Cdk5 or calpain activity in cells. Various cells and cell lines can be utilized for such screening assays, including cells specifically engineered for this purpose. Cells may be generated that express appropriate amounts Cdk5, NR2B, calpain, spectrin, and/or p35 under regulatable promoters. For example, cells that constitutively express two or more of these products are contemplated. Depending on the assay, culture may be required.

As with in vitro assays, one may assess binding or protein function, i.e., enzyme activity. Of particular relevance here are: (a) calpain-dependent p25 formation by Cdk5 cleavage of p35; (b) Cdk5-dependent spectrin cleavage by calpain; (c) Cdk5 phosphorylation.

D. Ex vivo Assays

The inventors also contemplate characterizing the effects of compounds which target Cdk5, NR2B and calpain interactions and regulatory mechanisms in cells and tissue acutely prepared from animal models. For example, brain tissue can be rapidly dissected and stabilized so that neuropharmacological and neurophysiologial experiments can be conducted to assess the effects of the compounds. Analyses may include alternations in signal transduction pathways as assessed by quantitative immunoblotting with phosphorylation state-specific antibodies. In this way, the effects of disrupting these regulatory mechanisms on signal transduction pathways can be assessed. In other experiments, the effect of these compounds upon electrophysiological parameters of fields of neurons or individual patch-clamped neurons may be assessed. Such analyses includes evaluation of synaptic plasticity as assessed by measurement of long-term potentiation (LTP) and long-term depression (LTD), which the inventors have discovered are under the control of these regulatory interactions involving Cdk5. Other analysis will include the firing properties and excitability of neurons and effects on individual ion conducting channels that control membrane potential and mediate action potential generation.

E. In vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance (s), identifies the substance as a useful compound. As a few examples, the effects of the compounds on various aspects of animal behavior will be assessed. These will include general assessment and assays designed to evaluate particular features including, learning, anxiety, depression, reward, locomotion, social inteaction, diet, food intake, and noceception, Effects on metabolic and endocrinological parameters will be assessed. The effect of compounds upon models of diseases will be assessed. In this manner, these studies may be viewed as the initial stages in the development of compounds as theraputic treatments for humans. In vivo screens are likely to be considered as secondary screens for compounds identified using cell free, in vitro and in cyto studies.

Treatment of animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal installation, bronchial installation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

F. Co-Immunoprecipitation

Protein-protein interactions may also be studied by using biochemical techniques such as cross-linking, co-immunoprecipitation, co-fractionation by chromatography, and "pull-down" assays, which are well known to those skilled in the art. The co-immunoprecipitation technique consists of (i) generating a cell lysate; (ii) adding an antibody to the cell lysate; (iii) precipitating and washing the antigen; and (iv) eluting and analyzing the bound proteins (Phizicky and Fields, 1995). The antigen used to generate the antibody can be a purified protein, or a synthetic peptide coupled to a carrier. Both monoclonal and polyclonal antibodies can be utilized in co-immunoprecipitation, or alternatively, a protein can be used which carries an epitope tag recognized by a commercially available antibody. An in vitro correlate pull-down assay may also be used where the purified protein is immobilized on a resin via covalent crosslinking or through affinity interactions with a moiety presented by the resin (e.g., nickel-NTA). Ligand protein may be added to the immobilized protein and binding may be monitored via immunodetection, or scintillation counting if the ligand is radiolabeled.

G. Fluorescence Energy Transfer (FRET)

FRET is a phenomenon in which the excited-state energy in one molecule (called the donor) is transferred to another molecule by a radiationless coupling. This mechanism was first correctly described by Förster, and differs from other types of energy transfer, such as electron sharing (Dexter) or trivial transfer (emission of a photon from the donor and reabsorption by the acceptor). The Dexter mechanism requires the two molecules to be in physical contact, while trivial transfer is a very low probability. In contrast, the För-ster mechanism exhibits a high probability when the two molecules are within the Förster radius, which is defined for any given pair of fluorophores.

The overall FRET efficiency depends on the Förster radius, and is determined by several factors and is directly related to the amount of overlap between the absorption spectra of the acceptor molecule and the emission spectra of the donor molecule. The amount of FRET also depends on the alignment of the donor and acceptor molecules, although most biological systems are not ridgidly aligned. The FRET efficiency is also affected by the ability of the acceptor molecule to absorb light, as indicated by its molar extinction coefficient, and the overall stability of the excited state of the donor molecule, as indicated by the probability that absorption will lead to fluorescence (quantum yield) and the lifetime of the excited state.

FRET between two different fluorophores can be assayed by several methods: looking at the change in color of the fluorescence, measuring the fluorescence lifetime of the donor, examining the changes upon photobleaching either the donor or acceptor, or as we show in this new invention: by measuring the fluorescence polarization of the acceptor. Regardless of the approach, most of these assays share common features of the instrumentation.

The types of the microscope used to measure FRET can be suitably selected depending the purpose. If frequent observations are necessary for monitoring a time course of the changing, conventional incident-light fluorescent microscope is preferred. If resolution is to be increased as in the case where detailed intercellular localization is to be monitored, confocal laser microscope is preferred. As a microscope system, an inverted microscope is preferred for most live cell measurements in view of keeping the physiological state of cell and preventing contamination. When an upright microscope is used, a water immersion lens can be used in the case of using lens of high power.

The filter set can be suitably selected depending on the fluorescent wave length of the fluorescent protein. For the observation of GFP, it is preferred to use a filter with excitation light of about 470-490 nm and fluorescent light of about 500-520 nm. For the observation of YFP, it is preferred to use a filter with excitation light of about 490-510 nm and fluorescent light of about 520-550 nm. For the observation of CFP, it is preferred to use a filter with excitation light of about 425 nm and fluorescent light of about 460-500 nm. For the purposes set forth herein, there are no specific requirements in terms of microscopes and filters, except that it would be useful to minimize the use of depolarizing elements in the light path. Microscope manufacturers all market strain-free optics for polarized light measurements in transmission and reflection microscopy, and such optics would be helpful for these polarized fluorescence measurements as well.

Moreover, when time course observation is carried out in living cells by using a fluorescent microscope, the cells should be photographed in a short period, and therefore a high sensitive cooled CCD camera is used. By using a cooled CCD camera, thermal noise can be decreased by cooling CCD, and weak fluorescent image can be clearly acquired by exposure of short period. Confocal microscopes can also be used for live cell imaging, as long as care is taken to minimize the exposure times.

An adaptation of FRET is bioluminescence resonance energy transfer or BRET. BRET utilizes an enhanced variant of YFP, citrine, and Renilla luciferase to reveal strong resonance energy transfer from the active luciferaase to the YFP, thereby invoking invoke epifluourescence. The advantage of BRET over FRET is that exogenous excitation is not required and multiple cells can be used to derive the binding data, although the emission energy is substantially less than FRET. BRET in live cells is conducted in 96-well plates using a standard plate reader with fluorescence detection capability (Jiang et al., 2007).

H. Phosphorylation Assays

Cdk5 phosphorylation activity assays may generally comprise $^{32}$P-incoporation into substrates as determined by phosphorimager analysis. Alternatively, phosphorylation may be detected by either Western blot or ELISA using a control Cdk5 substrate and a phosphorylation state-specific antibody to a Cdk5 phosphorylation site on the substrate. Also, mass spectrometry of phosphorylated substrates may also be performed.

I. Protease Assays

Calpain activity assays may generally comprise a reaction in which in the presence of $Ca^{2+}$ and the appropriate buffer conditions calpain cleaves a substrate. Cleavage may be detected by SDS-PAGE and protein staining, Western blot, or ELISA using an antibody specific for the cleaved or uncleaved substrate.

J. Immunodetection

Immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999), Gulbis and Galand (1993), De Jager et al. (1993), and Nakamura et al. (1987).

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Enzyme-linked immunosorbent assays (ELISAs) utilize antibodies to detect one or both members of a complex (e.g., calpain and Ckd5, Cdk5 and p25, Cdk5 and NR2B). Antibodies binding to one member of the complex may be immobilized onto a selected surface exhibiting protein affinity, such as a well in a polystyrene microtiter plate. Then, a composition having the antigen(s) is added to the wells. After binding and washing to remove non-specifically bound immune complexes, the bound antigen(s) may be detected. Detection may be achieved by the addition of a labeled antibody directed to the second member of the complex. This type of ELISA is a simple "sandwich ELISA." Detection may also be achieved by the addition of a third labeled antibody that binds the second antibody. Other formats may be applied as well.

Irrespective of the format employed, ELISAs have certain features in common, such as coating, incubating and binding, washing to remove non-specifically bound species, and detecting the bound immune complexes. For example, in coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Generally, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

III. Protein Purification

It may be desirable to purify various proteins (e.g., Cdk5, p35, p25, calpain, NR2B, etc.) for use in the screening assays discussed above. The starting material for such purifications may include tissues in which the proteins are endogenously expressed or preparations of prokaryotic or eukaryotic cells in which the proteins are expressed in recombinant form as result of molecular biology engineering. Protein purification techniques are well known to those of skill in the art. These techniques involve, at one level, the crude fractionation of the cellular milieu to polypeptide and non-polypeptide fractions. Such methods may include physical disruption followed by centrifugation, solvent extraction, salting-out (e.g., by ammonium sulfate or the like), desalting, precipitation, etc.

Having thus separated generally the polypeptide from other molecules, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

The term "purified protein" as used herein is intended to refer to a proteinaceous composition, isolated from other components, wherein the protein or peptide is purified to any degree relative to its naturally-obtainable state. A purified protein or peptide therefore also refers to a protein or peptide, free from the environment in which it may naturally occur. Generally, "purified" will refer to a protein composition that has been subjected to fractionation to remove various other components, and which composition substantially retains its expressed biological activity. Where the term "substantially purified" is used, this designation will refer to a composition in which the protein forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

There is no general requirement that the protein always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al, 1977). It will therefore be appreciated that under differing electrophoresis conditions, the apparent molecular weights of purified or partially purified expression products may vary.

High performance liquid chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

IV. Examples

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 2:
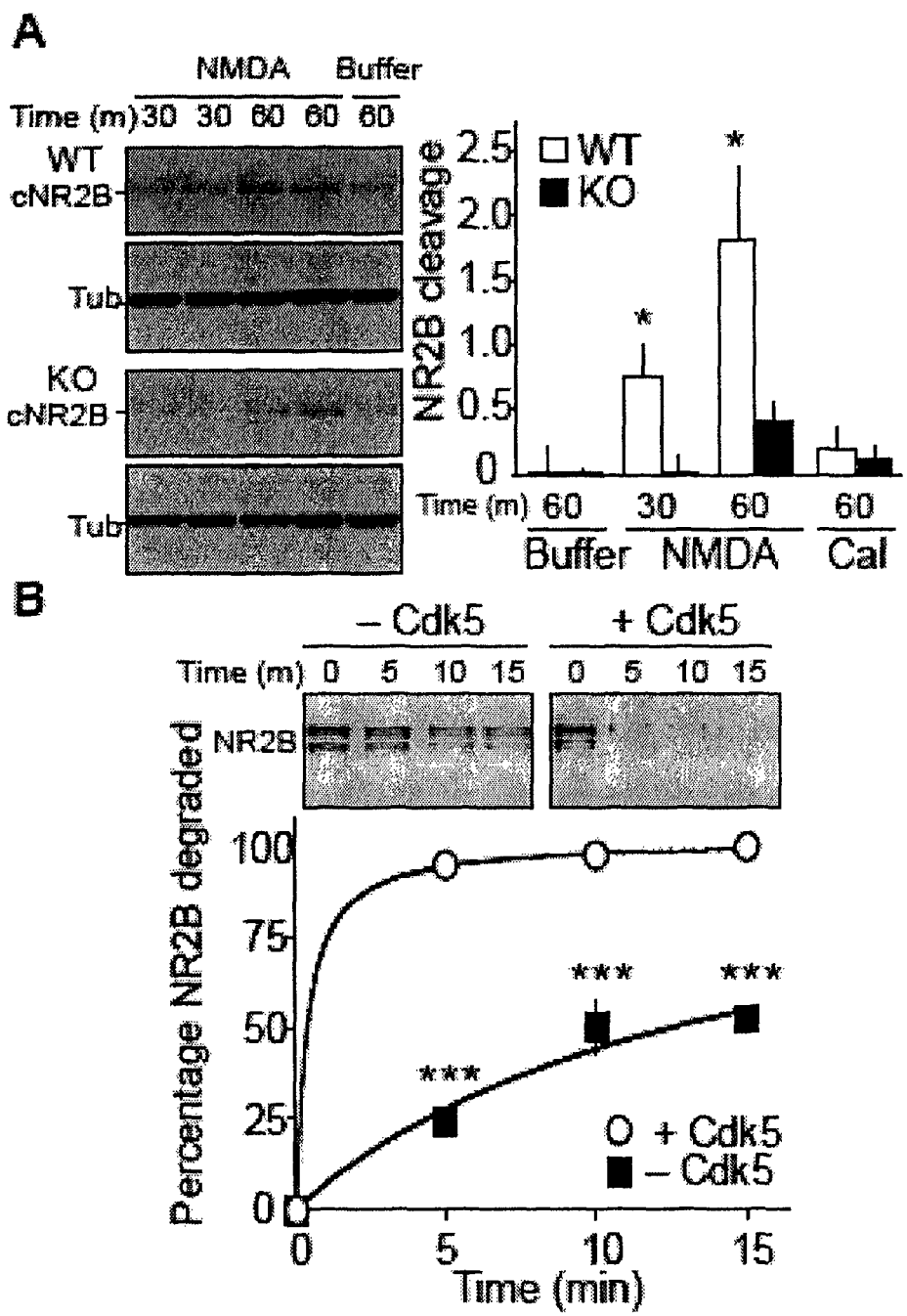
FIGS. 2A-B—Cdk5 activates calpain cleavage of the NR2B subunit of the NMDA receptor.
Figure 3:
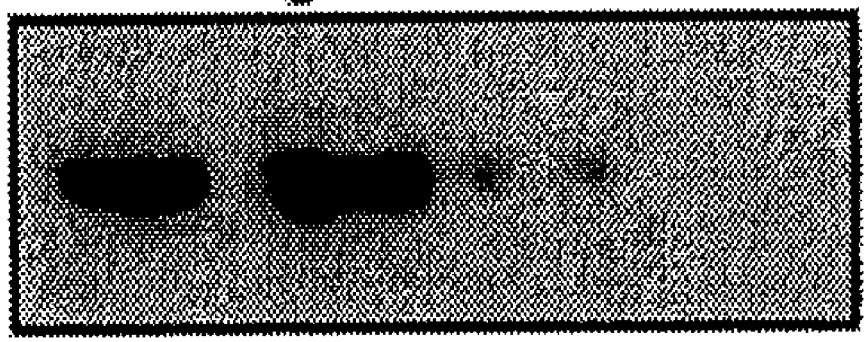
FIG. 3—Cdk5 binds calpain. An immunoblot is shown for calpain pulled down by recombinant Cdk5 bound to Ni2+-NTA resin in the presence or absence of recombinant NR2B.

The inventors found that loss of Cdk5 via conditional knock-out (CKO) resulted in elevated NR2B levels and reduced cleavage of NR2B by calpain in response to NMDA receptor activation (Hawasli et al., 2007) (FIG. 2A). This prompted them to conduct in vitro calpain cleavage assays with recombinant cytoplasmic domain of NR2B. Addition of Cdk5 caused a dramatic increase in calpain activity that was not dependent upon Cdk5 activity (FIG. 2B). Furthermore, Cdk5 phosphorylated neither NR2B nor calpain, suggesting the activation was based on protein-protein interactions. In vitro pull down assays demonstrated that calpain bound strongly to Cdk5 (FIG. 3). Other experiments demonstrated that calpain coimmunoprecipitated with Cdk5 in hippocampal lysates (Hawasli et al., 2007). Thus, Cdk5 both activates and directly binds calpain. Cdk5 was also found to bind to NR2B, and thus serves a scaffolding function linking calpain to NR2B.

Figure 4:
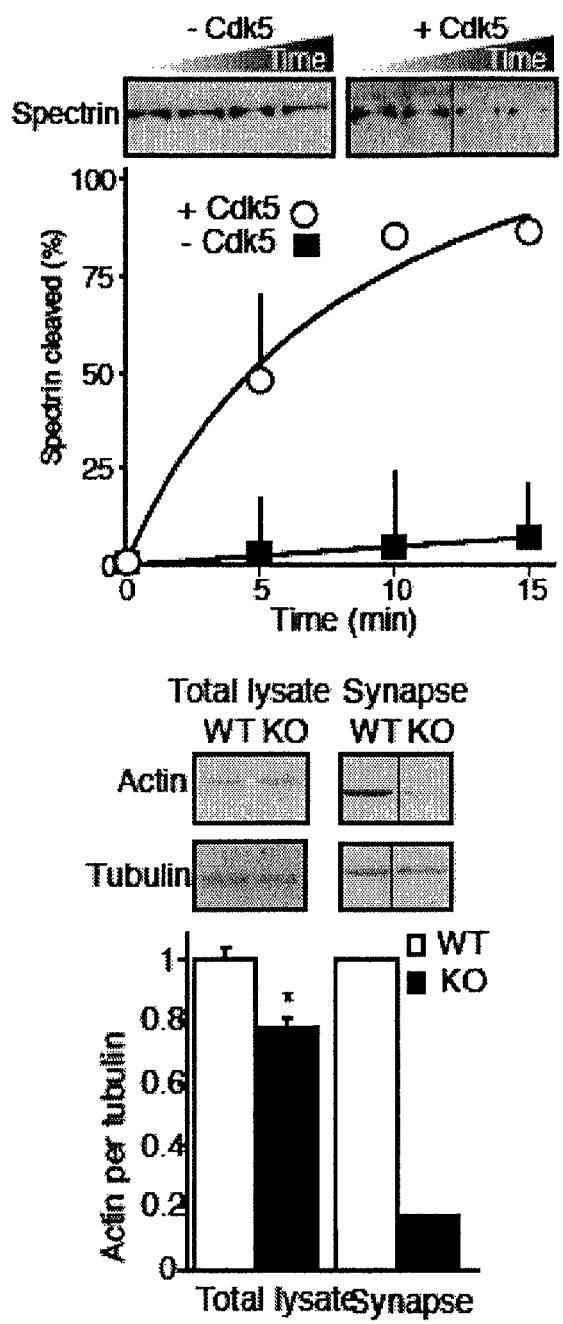
FIG. 4—Activation of spectrin cleavage by calpain in vitro (top) and dramatic reduction in unpolymeerized actin levels in response to Cdk5 conditional knockout (bottom) shown with representative bands and quantitation.

The inventors next sought to assess whether Cdk5 might serve as a general synaptic activator of calpain. To evaluate this possibility, they repeated the calpain activation assay using spectrin as a substrate (FIG. 4). Indeed, Cdk5 activated calpain cleavage of spectin in a very similar manner to that observed with NR2B. Based on this observation, they predicted that CKO of Cdk5 would result in a reduction in the stabilization of actin filaments. Indeed, the inventors detected a dramatic reduction in unpolymerized synaptic actin) in Cdk5 CKO mice.

Example 2

Figure 6:
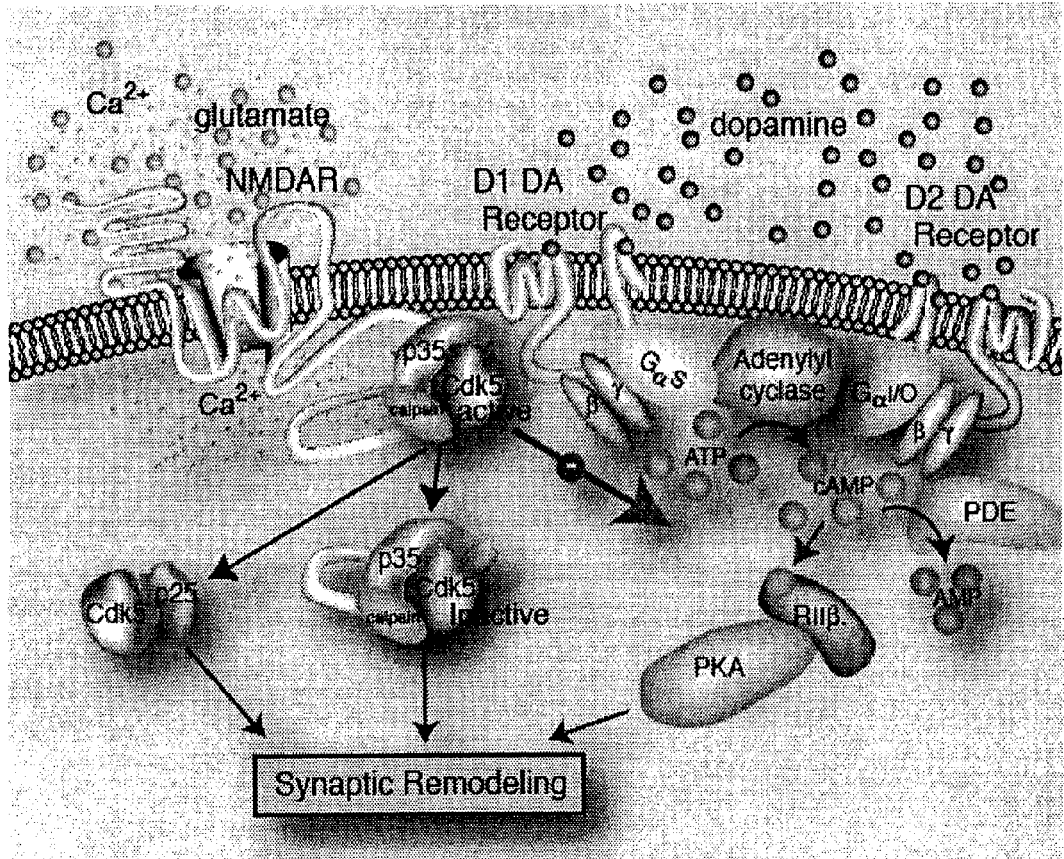
FIG. 6—Schematic model depicting the regulation of Cdk5 by NMDA receptors, Cdk5's regulation of PKA signaling, regulation of calpain by Cdk5, and how these pathways converge upon synaptic remodeling.

The inventors hypothesized that activation of NMDA receptors results in inactivation of Cdk5 and concomitant cleavage of the NMDA receptor releasing the NR2B/Cdk5/calpain complex. To fully understand the significance of this Cdk5 regulatory mechanism, it is useful to point out that the inventors previously demonstrated that Cdk5 provides a negative tonus toward G-protein-coupled receptor (GPCR)/cAMP/PKA signaling. They also have shown two pathways by which this is accomplished: via the phosphorylation of the protein phosphatase-1 inhibitors, DARPP-32 (Bibb et al., 1999 (and inhibitor-1 (Nguyen et al., 2007b; Bibb et al., 2001b). The inventors also have identified a number of novel pathways by which Cdk5 further dampens the GPC/cAMP/PKA pathway (unpublished results). They hypothesize that glutatergic neurotransmission inactivates Cdk5 which mediates alterations in NMDA receptor constituency and actin dynamics via activation of calpain (FIG. 6). Concomitantly, this results in a potention in PKA signaling through the inactivation of Cdk5, resulting in the activation of additional signaling pathways that contribute to synaptic remodeling. In this manner, Cdk5 serves to couple the two key second messagers $Ca^{2+}$ and cAMP upon which synaptic plasticity, learning and memory depend.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference:

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
Angelo et al., *J. Neurochem.* 99:353-70, 2006.
Ben-Zeev et al., *Methods Mol. Biol.* 109:215-37, 1999.
Bibb et al., *Nature* 402:669-71, 1999
Bibb et al., *Nature* 410:376-80, 2001a.
Bibb et al., *J. Biol. Chem.* 276:14490-14497, 2001b.
Bibb, J. A., *Neurosignals* 12:191-199, 2003.
Capaldi et al., *Biochem. Biophys. Res. Comm.*, 74(2):425-433, 1977.
Cheung et al., *Neuron* 50:13-18, 2006.
Cruz & Tsai, *Curr. Opin. Neurobiol.* 14:390-394, 2004.
Cruz et al., *Neuron* 40:471-83, 2003.
De Jager et al., *Semin. Nucl. Med.* 23(2):165-79, 1993.
Fischer et al., *Neuron* 48:825-38, 2005.
Gulbis and Galand, *Hum. Pathol.* 24(12):1271-85, 1993.
Guo, Q., *Sci. Aging Knowledge Environ.*, 50:36, 2003.
Hawasli et al., *Nature Neurosci.* (in press), 2007.
Jiang et al., *J. Biol. Chem.* 282:10576-84, 2007.
Kusakawa et al., *J. Biol. Chem.* 275:17116-172, 2000.

Lee et al., *Nature* 405:360-364, 2000.
Liu et al., *Biochem. J.* 394:715-25, 2006.
Lynch et al., *Neuropharmacol.* 52:12-23, 2007.
Nakamura et al., In: *Enzyme Immunoassays: Heterogeneous and Homogeneous Systems*, Chapter 27, 1987.
Nguyen & Bibb, *J. Cell. Biol.* 163:697-99, 2003.
Nguyen et al., *J. Neurochem.* (in press), 2007a.
Nguyen et al., *J. Biol. Chem.* (epub ahead of print March 30), 2007b.
Ohshima et al., *Proc. Nat'l Acad. Sci. USA* 93:11173-78, 1996.
Phizicky and Fields, *Microbiol Rev.* 59(1):94-123, 1995.
Sahin & Bibb, *Proc. Nat'l Acad. Sci. USA* 101:112-113, 2004.

What is claimed is:

1. A method of identifying an inhibitor of calpain activation comprising:
   (a) providing a system comprising calpain and Cdk5;
   (b) introducing into said system a candidate substance; and
   (c) assessing Cdk5/calpain complex formation, wherein assessing comprises measuring Cdk5 binding to calpain, and
   wherein a candidate substance that reduces Cdk5/calpain complex formation, as compared to Cdk5/calpain complex formation observed in the absence of said candidate substance, identifies said candidate substance as an inhibitor of calpain activation.

2. The method of claim 1, wherein said system is a cell-free system.

3. The method of claim 1, wherein said system is a cell-based system.

4. The method of claim 1, wherein measuring binding comprises gel mobility shift, FRET, BRET, Western blot, protein pull-down, or ELISA-based detection of complex formation.

5. The method of claim 2, wherein said cell-free system is derived from a cell selected from the group consisting of continuously dividing cells in culture, primary cultures of neurons derived from animal brain tissue, or neurons either acutely dissociated from or occurring in intact brain tissue.

6. The method of claim 3, wherein said cell-based system is based on a cell selected from the group consisting of continuously dividing cells in culture, primary cultures of neurons derived from animal brain tissue, or neurons acutely dissociated from intact brain tissue.

* * * * *